(12) United States Patent
Bassinger et al.

(10) Patent No.: US 8,070,711 B2
(45) Date of Patent: Dec. 6, 2011

(54) THERMAL MANAGEMENT ALGORITHM FOR PHACOEMULSIFICATION SYSTEM

(75) Inventors: Kenneth D. Bassinger, Fort Worth, TX (US); Mikhail Boukhny, Laguna Niguel, CA (US); Michael D. Morgan, Costa Mesa, CA (US); Ahmad Salehi, Irvine, CA (US); Dan Teodorescu, Fountain Valley, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 9 days.

(21) Appl. No.: 12/634,283

(22) Filed: Dec. 9, 2009

(65) Prior Publication Data

US 2011/0137232 A1 Jun. 9, 2011

(51) Int. Cl.
*A61F 9/007* (2006.01)
*G06F 1/26* (2006.01)
(52) U.S. Cl. .......................... 604/22; 700/295
(58) Field of Classification Search .............. 604/22, 604/289, 294, 297, 298, 300; 700/295
See application file for complete search history.

(56) References Cited

U.S. PATENT DOCUMENTS

| | | | |
|---|---|---|---|
| 3,526,219 A | 9/1970 | Balamuth |
| 3,589,363 A | 6/1971 | Banko |
| 3,601,126 A | 8/1971 | Estes et al. |
| 3,693,613 A | 9/1972 | Kelman |
| 3,812,855 A | 5/1974 | Banko |
| 3,812,858 A | 5/1974 | Oringer |
| 3,857,387 A | 12/1974 | Shock |
| 3,902,495 A | 9/1975 | Weiss et al. |
| 3,930,505 A | 1/1976 | Wallach |
| 3,942,519 A | 3/1976 | Shock |
| 3,952,732 A | 4/1976 | Shock |
| 3,956,826 A | 5/1976 | Perdreaux, Jr. |
| 3,964,487 A | 6/1976 | Judson |
| 3,990,452 A | 11/1976 | Murry et al. |
| 4,024,467 A | 5/1977 | Andrews et al. |
| 4,024,866 A | 5/1977 | Wallach |
| 4,114,623 A | 9/1978 | Meinke et al. |
| 4,126,137 A | 11/1978 | Archibald |
| 4,156,187 A | 5/1979 | Murry et al. |

(Continued)

FOREIGN PATENT DOCUMENTS

EP 359217 3/1990

(Continued)

OTHER PUBLICATIONS

Jiromaru Tsujino, "Ultrasonic Motor Using a One-Dimensional Longitudinal-Torsional Vibration Converter With Diagonal Slits", Smart Mater, Struct. 7 (1998); pp. 345-351.

(Continued)

*Primary Examiner* — Jackie Ho
*Assistant Examiner* — Michael J Anderson
(74) *Attorney, Agent, or Firm* — Kenneth D. Bassinger (57) ABSTRACT

A control system for managing power supplied to a phacoemulsification hand piece includes a power source that provides power to the hand piece and a controller that controls the power source. The controller calculates a thermal value based on irrigation fluid flow and a power level and decreases the power level in proportion to the calculated thermal value when the calculated thermal value exceeds a threshold thermal value. Irrigation fluid flow can be calculated from irrigation fluid pressure.

21 Claims, 8 Drawing Sheets

U.S. PATENT DOCUMENTS

| | | | |
|---|---|---|---|
| 4,168,707 | A | 9/1979 | Douvas et al. |
| 4,184,510 | A | 1/1980 | Murry et al. |
| 4,223,676 | A | 9/1980 | Wuchiinich et al. |
| 4,246,902 | A | 1/1981 | Martinez |
| 4,248,232 | A | 2/1981 | Engelbrecht et al. |
| 4,406,284 | A | 9/1983 | Banko |
| 4,417,578 | A | 11/1983 | Banko |
| 4,493,694 | A | 1/1985 | Wuchinich |
| 4,496,342 | A | 1/1985 | Banko |
| 4,504,264 | A | 3/1985 | Kelman |
| 4,508,532 | A | 4/1985 | Drews et al. |
| 4,515,583 | A | 5/1985 | Sorich |
| 4,589,415 | A | 5/1986 | Haaga |
| 4,590,935 | A | 5/1986 | Ranalli |
| 4,609,368 | A | 9/1986 | Datson, Jr. |
| 4,651,280 | A | 3/1987 | Chang et al. |
| 4,658,819 | A | 4/1987 | Harris et al. |
| 4,705,500 | A | 11/1987 | Reimels et al. |
| 4,712,544 | A | 12/1987 | Ensslin |
| 4,739,759 | A | 4/1988 | Rexroth et al. |
| 4,750,488 | A | 6/1988 | Wuchinich et al. |
| 4,770,654 | A | 9/1988 | Rogers et al. |
| 4,793,346 | A | 12/1988 | Mindich |
| 4,827,911 | A * | 5/1989 | Broadwin et al. .................. 601/4 |
| 4,869,715 | A | 9/1989 | Sherburne |
| 4,922,902 | A | 5/1990 | Wuchinich et al. |
| 4,961,424 | A | 10/1990 | Kubata et al. |
| 4,969,885 | A | 11/1990 | Farin |
| 4,989,583 | A | 2/1991 | Hood |
| 4,989,588 | A | 2/1991 | Kubata et al. |
| 5,026,387 | A | 6/1991 | Thomas |
| 5,116,343 | A | 5/1992 | Ames et al. |
| 5,139,509 | A | 8/1992 | Fischer et al. |
| 5,151,085 | A | 9/1992 | Sakurai et al. |
| 5,154,694 | A | 10/1992 | Kelman |
| 5,154,696 | A | 10/1992 | Shearing |
| 5,160,317 | A | 11/1992 | Costin |
| 5,180,363 | A | 1/1993 | Idemoto et al. |
| 5,188,102 | A | 2/1993 | Idemoto et al. |
| 5,188,589 | A | 2/1993 | Wypych et al. |
| 5,205,817 | A | 4/1993 | Idemoto et al. |
| 5,222,959 | A | 6/1993 | Anis |
| 5,242,385 | A | 9/1993 | Strukel |
| 5,279,547 | A | 1/1994 | Costin |
| 5,304,115 | A | 4/1994 | Pflueger et al. |
| 5,342,293 | A | 8/1994 | Zanger |
| 5,359,996 | A | 11/1994 | Hood |
| 5,431,664 | A | 7/1995 | Ureche et al. |
| 5,445,637 | A * | 8/1995 | Bretton ........................... 606/41 |
| 5,520,633 | A | 5/1996 | Costin |
| 5,569,188 | A | 10/1996 | Mackool |
| 5,591,127 | A | 1/1997 | Barwick, Jr. et al. |
| 5,676,649 | A | 10/1997 | Boukhny et al. |
| 5,700,240 | A | 12/1997 | Barwick, Jr. et al. |
| 5,722,945 | A | 3/1998 | Anis et al. |
| 5,733,256 | A | 3/1998 | Costin |
| 5,766,146 | A | 6/1998 | Barwick, Jr. et al. |
| 5,808,396 | A | 9/1998 | Boukhny |
| 5,865,790 | A | 2/1999 | Bair |
| 6,027,515 | A | 2/2000 | Cimino |
| 6,028,387 | A | 2/2000 | Boukhny |
| 6,077,285 | A | 6/2000 | Boukhny |
| 6,083,193 | A * | 7/2000 | Kadziauskas et al. .......... 604/22 |
| 6,175,180 | B1 | 1/2001 | Angelini et al. |
| 6,179,805 | B1 | 1/2001 | Sussman et al. |
| 6,179,808 | B1 | 1/2001 | Boukhny et al. |
| 6,193,683 | B1 * | 2/2001 | Ludin et al. ..................... 604/22 |
| 6,261,283 | B1 | 7/2001 | Morgan et al. |
| 6,261,297 | B1 | 7/2001 | Kadziauskas et al. |
| 6,283,974 | B1 | 9/2001 | Alexander |
| 6,315,755 | B1 | 11/2001 | Sussman |
| 6,394,974 | B1 | 5/2002 | Kadziauskas et al. |
| 6,402,769 | B1 | 6/2002 | Boukhny |
| 6,629,948 | B2 * | 10/2003 | Rockley et al. ................. 604/22 |
| 6,699,212 | B1 * | 3/2004 | Kadziauskas et al. .......... 604/22 |
| 6,780,165 | B2 | 8/2004 | Kadziauskas |
| 6,892,057 | B2 | 5/2005 | Nilsson |
| 7,374,552 | B2 | 5/2008 | Wuchinich |
| 2001/0001123 | A1 | 5/2001 | Madan et al. |
| 2001/0011176 | A1 | 8/2001 | Boukhny |
| 2002/0193817 | A1 * | 12/2002 | Lal et al. ....................... 606/169 |
| 2003/0045887 | A1 | 3/2003 | Sakurai et al. |
| 2004/0092800 | A1 | 5/2004 | Mackool |
| 2004/0092922 | A1 * | 5/2004 | Kadziauskas et al. .......... 606/27 |
| 2004/0215127 | A1 * | 10/2004 | Kadziauskas et al. .......... 604/22 |
| 2005/0054971 | A1 * | 3/2005 | Steen et al. ..................... 604/22 |
| 2005/0209621 | A1 | 9/2005 | Gordon et al. |
| 2006/0041200 | A1 | 2/2006 | Dotter et al. |
| 2008/0139994 | A1 | 6/2008 | Mackool et al. |

FOREIGN PATENT DOCUMENTS

| | | |
|---|---|---|
| WO | WO 92/07622 | 5/1992 |
| WO | WO 99/18901 | 4/1999 |
| WO | WO 01/41672 | 6/2001 |
| WO | WO 2004/080505 A2 | 9/2004 |

OTHER PUBLICATIONS

Shuyu, Lin "Sandwiched Piezoelectric Ultrasonic Transducers of Longitudinal-Torsional Compound Vibrational Modes." IEEE Transactions of Ultrasonic, Ferroelectrics and Frequency Control, Nov. 1997, pp. 1189-1197.

* cited by examiner

(Prior Art)

THERMAL MANAGEMENT ALGORITHM FOR PHACOEMULSIFICATION SYSTEM

BACKGROUND OF THE INVENTION

The present invention relates to phacoemulsification surgery and more particularly to a thermal management algorithm in which the amplitude of power applied to a phacoemulsification hand piece is varied in proportion to temperature.

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. A typical surgical hand piece suitable for phacoemulsification procedures consists of an ultrasonically driven phacoemulsification hand piece, an attached hollow cutting needle surrounded by an irrigating sleeve, and an electronic control console. The hand piece assembly is attached to the control console by an electric cable and flexible tubing. Through the electric cable, the console varies the power level transmitted by the hand piece to the attached cutting needle. The flexible tubing supplies irrigation fluid to the surgical site and draws aspiration fluid from the eye through the hand piece assembly.

The operative part in a typical hand piece is a centrally located, hollow resonating bar or horn directly attached to a set of piezoelectric crystals. The crystals supply the required ultrasonic vibration needed to drive both the horn and the attached cutting needle during phacoemulsification, and are controlled by the console. The crystal/horn assembly is suspended within the hollow body or shell of the hand piece by flexible mountings. The hand piece body terminates in a reduced diameter portion or nosecone at the body's distal end. Typically, the nosecone is externally threaded to accept the hollow irrigation sleeve, which surrounds most of the length of the cutting needle. Likewise, the horn bore is internally threaded at its distal end to receive the external threads of the cutting tip. The irrigation sleeve also has an internally threaded bore that is screwed onto the external threads of the nosecone. The cutting needle is adjusted so that its tip projects only a predetermined amount past the open end of the irrigating sleeve.

During the phacoemulsification procedure, the tip of the cutting needle and the end of the irrigation sleeve are inserted into the anterior capsule of the eye through a small incision in the outer tissue of the eye. The surgeon brings the tip of the cutting needle into contact with the lens of the eye, so that the vibrating tip fragments the lens. The resulting fragments are aspirated out of the eye through the interior bore of the cutting needle, along with irrigation solution provided to the eye during the procedure, and into a waste reservoir.

Throughout the procedure, irrigating fluid is pumped into the eye, passing between the irrigation sleeve and the cutting needle and exiting into the eye at the tip of the irrigation sleeve and/or from one or more ports, or openings, cut into the irrigation sleeve near its end. The irrigating fluid protects the eye tissues from the heat generated by the vibrating of the ultrasonic cutting needle. Furthermore, the irrigating fluid suspends the fragments of the emulsified lens for aspiration from the eye.

Power is applied to the hand piece to vibrate the cutting needle. In general, the amplitude of needle movement (or vibration) is proportional to the power applied. In conventional phacoemulsification systems, the needle vibrates back and forth producing a longitudinal needle stroke. In improved systems, the needle may be caused to vibrate in a twisting or torsional motion. Regardless of the type of vibration, the magnitude of vibration (or amplitude of needle stroke) varies with applied power.

One complication that may arise during the procedure is burning of the cornea at the incision site. These corneal burns are caused by heating of the needle (and surrounding sleeve) at the corneal incision. The inventors have found that this heating is dependent on three basic factors: the amount of power applied to the hand piece (which in turn determines the magnitude of needle vibration or amplitude of needle stroke); the amount of fluid flow through the eye (since the fluid carries heat away); and the amount of friction between the needle and the surrounding sleeve at the incision (as can be appreciated, the tighter the fit between the sleeve and the needle, the more friction, and the more heat produced as the needle vibrates).

In other words, heat is produced at the corneal incision as the cutting needle rubs against the surrounding irrigation sleeve. This heat is normally dissipated by fluid flowing through irrigation sleeve, into the anterior chamber of the eye, and out of the eye through the aspiration lumen. The friction between the cutting needle and the sleeve at the corneal incision site can vary depending on the characteristics of the incision. Generally, a smaller incision (which is desirable from a surgical perspective) can lead to a greater friction force between the needle and the sleeve as the walls of the incision press the sleeve against the needle. In such a case, when the needle is vibrated, heat is produced. If the fluid flowing through the eye is insufficient (or if too much heat is produced), a corneal burn can result. Corneal burns are problematic because they distort the cornea resulting in distorted vision. Since cataract surgery has gravitated toward smaller and smaller incisions, the risk of corneal burns appears to be increasing.

SUMMARY OF THE INVENTION

In one embodiment consistent with the principles of the present invention, the present invention is a control system for managing power supplied to a phacoemulsification hand piece. The control system includes an irrigation pressure sensor, a power source that provides power to the hand piece, and a controller that controls the power source. The controller calculates a thermal value based on the irrigation pressure and a power level and decreases the power level in proportion to the calculated thermal value when the calculated thermal value exceeds a threshold thermal value.

In another embodiment consistent with the principles of the present invention, the present invention is a control system for managing power supplied to a phacoemulsification hand piece. The control system includes a power source that provides power to the hand piece and a controller that controls the power source. The controller calculates a thermal value based on irrigation fluid flow and a power level and decreases the power level in proportion to the calculated thermal value when the calculated thermal value exceeds a threshold thermal value. Irrigation fluid flow can be calculated from an irrigation pressure.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
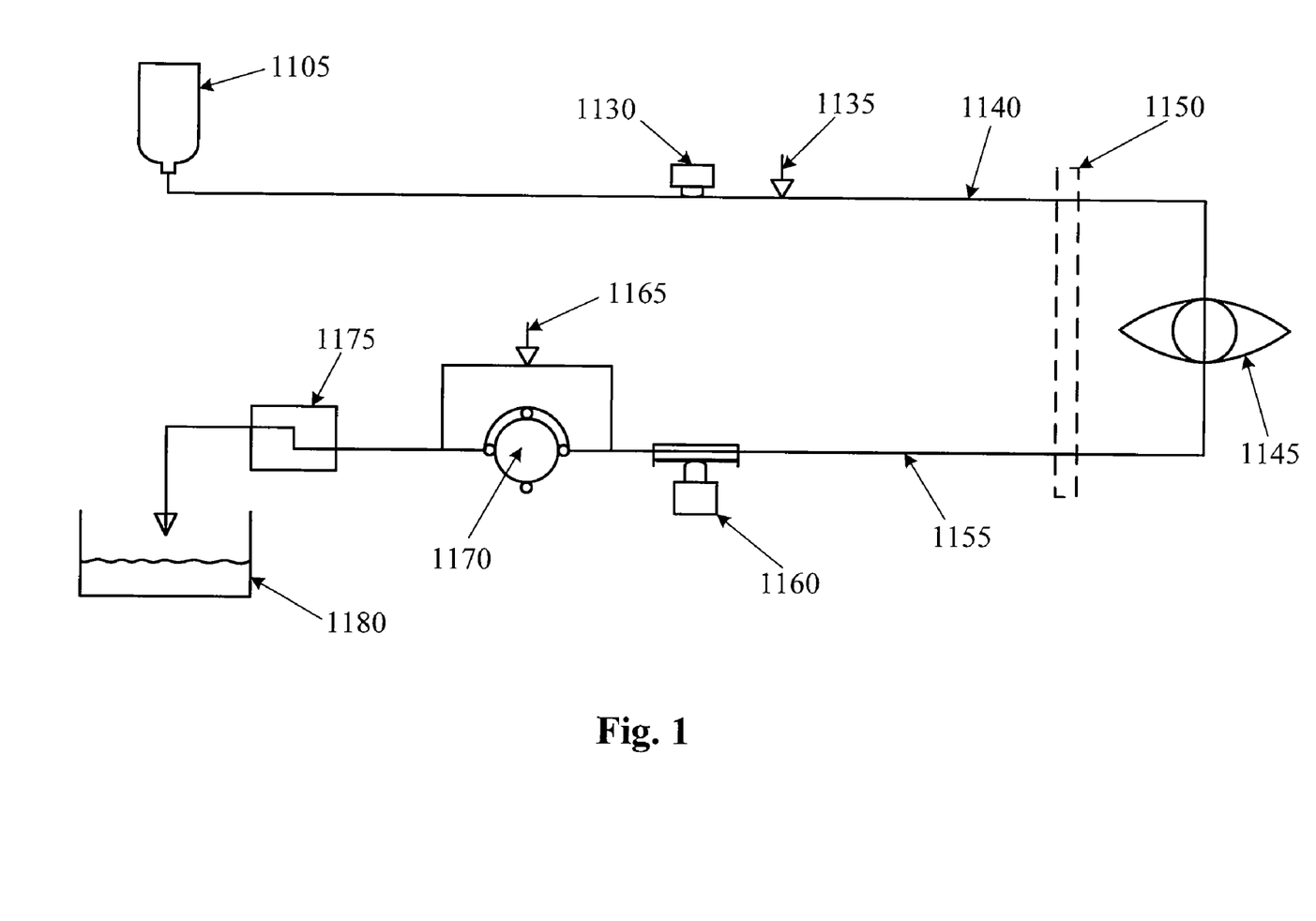
FIG. 1 is a diagram of the components in the fluid path of a phacoemulsification system.

In one embodiment of the present invention, FIG. 1 is a diagram of the components in the fluid path of a phacoemulsification system. FIG. 1 depicts the fluid path through the eye 1145 during cataract surgery. The components include an irrigation fluid source 1105, an irrigation pressure sensor 1130, an irrigation valve 1135, an irrigation line 1140, a hand piece 1150, an aspiration line 1155, an aspiration pressure sensor 1160, a vent valve 1165, a pump 1170, a reservoir 1175 and a drain bag 1180. The irrigation line 1140 provides irrigation fluid to the eye 1145 during cataract surgery. The aspiration line 1155 removes fluid and emulsified lens particles from the eye during cataract surgery.

When irrigation fluid exits irrigation fluid source 1105, it travels through irrigation line 1140 and into the eye 1145. An irrigation pressure sensor 1130 measures the pressure of the irrigation fluid in irrigation line 1140. An optional irrigation valve 1135 is also provided for on/off control of irrigation. Irrigation pressure sensor 1130 is implemented by any of a number of commercially available fluid pressure sensors and can be located any where in the irrigation fluid path (any where between the irrigation source 1105 and the eye 1145).

Figure 2:
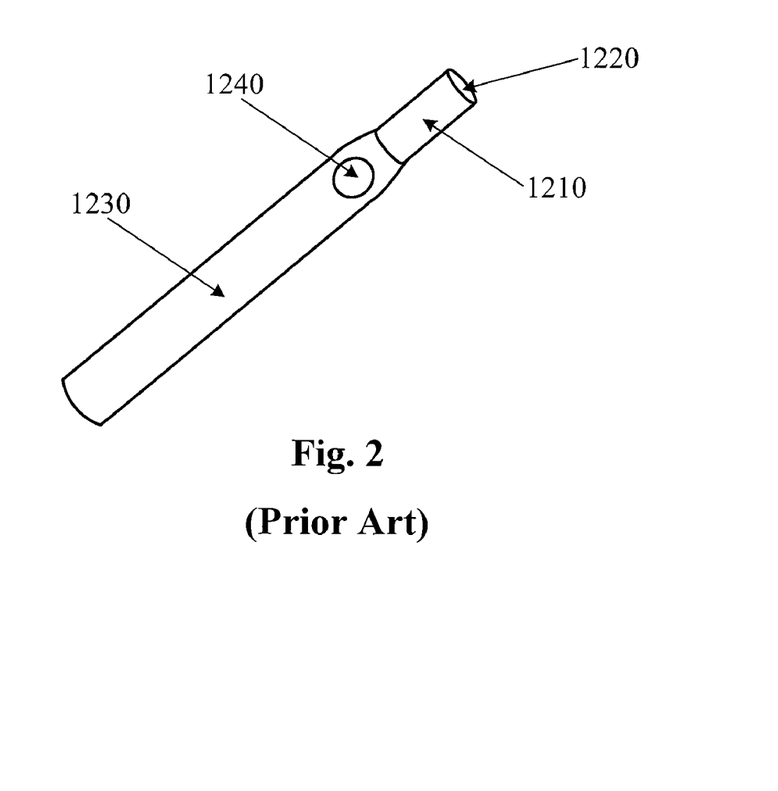
FIG. 2 is a perspective view of the distal end of a phacoemulsification needle and irrigation sleeve.

A hand piece 1150 is placed in the eye 1145 during a phacoemulsification procedure. The hand piece 1150 has a hollow needle (as seen in FIG. 2) that is ultrasonically vibrated in the eye to break up the diseased lens. A sleeve located around the needle provides irrigation fluid from irrigation line 1140. The irrigation fluid passes through the space between the outside of the needle and the inside of the sleeve (as more clearly shown in FIGS. 12 and 13). Fluid and lens particles are aspirated through the hollow needle. In this manner, the interior passage of the hollow needle is fluidly coupled to aspiration line 1155. Pump 1170 draws the aspirated fluid from the eye 1145. An aspiration pressure sensor 1160 measures the pressure in the aspiration line. An optional vent valve can be used to vent the vacuum created by pump 1170. The aspirated fluid passes through reservoir 1175 and into drain bag 1180.

FIG. 2 is a perspective view of the distal end of a prior art phacoemulsification hand piece. In FIG. 2, a phacoemulsification needle 1210 is surrounded by an irrigation sleeve 1230. The phacoemulsification needle 1210 has an open end 1220 through which lens particles are aspirated from the eye during cataract surgery. The irrigation sleeve 1230 has an optional opening 1240 through which irrigation fluid flows into the eye. The needle 1210 and sleeve 1230 are both inserted into the anterior chamber of the eye during cataract surgery. When power is applied to the hand piece, the needle 1210 vibrates ultrasonically. Friction between the needle 1210 and the sleeve 1230 can cause heating to occur—particularly at the incision site. A tight incision presses the sleeve 1230 against the needle 1210 which can lead to heating and potentially a corneal burn.

Figure 3:
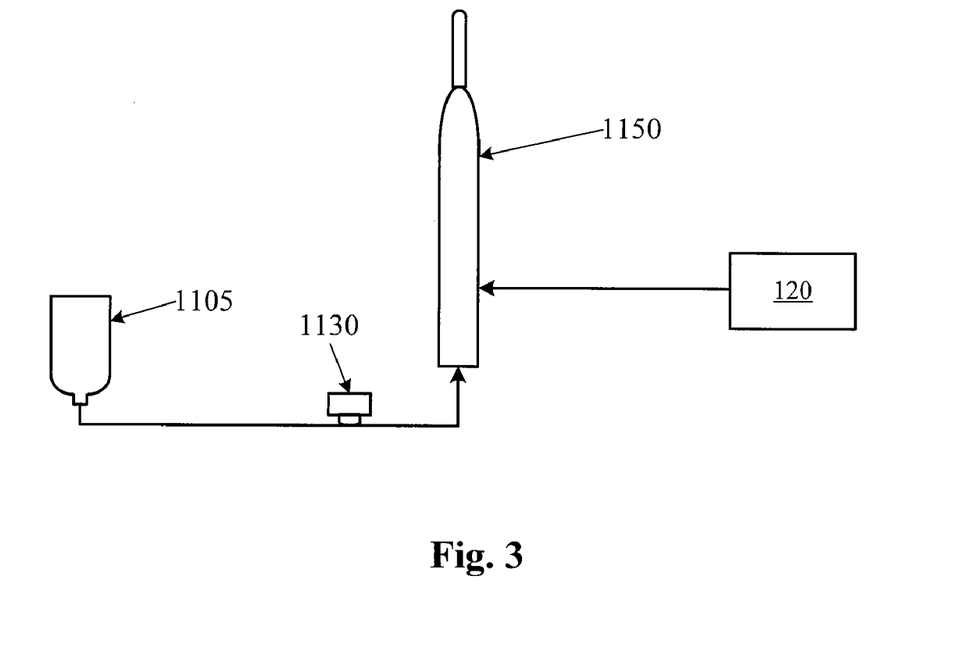
FIG. 3 is a diagram of a partial system according to the principles of the present invention.

FIG. 3 is a diagram of a partial system according to the principles of the present invention. In FIG. 3, irrigation fluid source provides irrigation fluid to hand piece 1150. An irrigation pressure sensor measures the pressure of the irrigation fluid. A power source 120 provides power to hand piece 1150. As previously described, power source 120 provides ultrasonic power to hand piece 1150 that vibrates the phacoemulsification needle.

Figure 4:
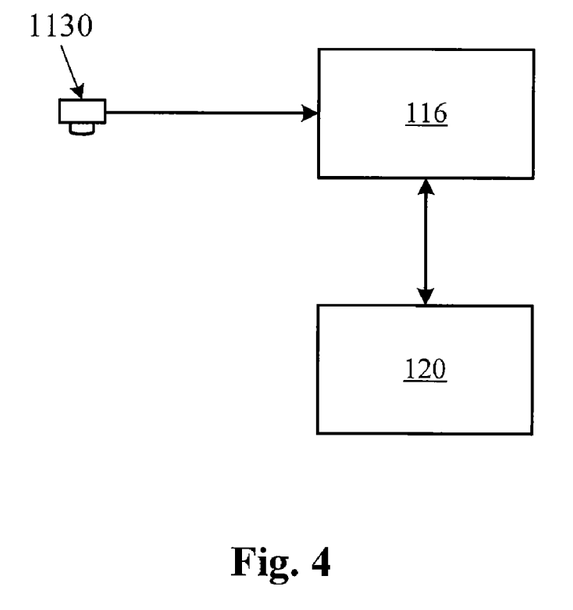
FIG. 4 is a block diagram of one embodiment of a control system according to the principles of the present invention.

FIG. 4 is a block diagram of one embodiment of a control system according to the principles of the present invention. In FIG. 4, CPU 116 is coupled to power source 120 and irrigation pressure sensor 1130. In this manner, CPU 116 receives pressure information from irrigation pressure sensor 1130. CPU 116 also interfaces with power source 120 and controls its operation—thereby controlling the power sent to the hand piece. As previously described, CPU 116 can be any suitable controller.

As previously described, unwanted heating can occur at the incision site when too much power is applied to the hand piece and too little irrigation fluid flows through the eye. Since the irrigation fluid carries heat away, when irrigation fluid flow is decreased (for example, when an occlusion occurs), heating can occur. Generally, the amount of heat generated is a function of the amount of power applied to the hand piece and the amount of irrigation fluid flow through the eye. Friction between the irrigation sleeve and the phacoemulsification needle is the primary source of heat. When the needle rubs against the sleeve, it produces heat. The amount of power applied to the hand piece is linearly related to the needle stroke—or the distance the needle travels. The more power applied, the more the needle travels (and the more the needle rubs against the sleeve).

Mathematically, if ΔT is the rise in the thermal value, then ΔT=T−T0, (where T0 is the thermal value of the eye and T is the actual thermal value around the needle as a function of time). Suppose that the thermal response to an ultrasonic pulse that happens at time t=0 of the total energy A is given by:

$$\Delta T(t) = AG(t)$$

where G(t) is the response function of the system. Then ΔT, the rise in thermal value, by heat generation in time Q(t) is given by:

$$\Delta T(t) = \int_{-\infty}^{t} Q(t)G(t)dt$$

The heat Q in the above equation accounts for both the heat generated by ultrasound power and the heat removed by the fluid flow. Hence, Q is proportional to ultrasound power and fluid flow.

Emprical studies have found the response function G(t) to be exponential as shown below.

$$G(t) = G_0 e^{-\alpha t}$$

The coefficients '$G_0$' and '$\alpha$' can be determined to best fit the coefficient of friction (between the sleeve and the needle) and experimental data on ΔT under various flow and power conditions.

In this manner, the calculated thermal value (T) is a function of: the power (P) applied to the hand piece, the fluid flow (F) through the eye, and the friction (Fr) between the needle and the sleeve. The fluid flow through the eye is calculated from the irrigation pressure (since the cross section area of the irrigation path is known, the flow through the irrigation line is calculated based on the irrigation fluid pressure as read from the irrigation pressure sensor). Therefore, T=F (P, F, Fr). This calculated thermal value provides a good estimate of the actual temperature experienced at the incision site (where burning is most likely to occur).

This calculated thermal value is used to implement a thermal watch algorithm. Since the calculated thermal value provides a good estimate of the actual temperature, a threshold thermal value can be set to trigger the algorithm. In other words, when the calculated thermal value exceeds the threshold thermal value, the algorithm can act to reduce the likelihood of heating (by decreasing power).

As seen in FIG. 4, the CPU 116 reads the irrigation pressure from the irrigation pressure sensor 1130. Since CPU 116 controls the power source 120, CPU 116 also has the value for the power level applied to the hand piece. CPU 116 uses these two values (in conjunction with the coefficient of friction) to calculate a temperature that estimates the actual temperature at the incision site. In this manner, CPU 116 continuously or periodically calculates T=f(P, F, Fr). The calculated thermal value is compared continuously or periodically to a threshold thermal value. When the calculated thermal value exceeds the threshold thermal value, the power to the hand piece is decreased.

In one embodiment of the present invention, the calculated thermal value is used as an input to control the amount of power provided to the hand piece. In this manner, the actual power applied to the hand piece tracks the inverse of the calculated thermal value when the calculated thermal value exceeds the threshold thermal value. This is more clearly seen with reference to FIGS. 6-10 below.

As described, the threshold thermal value (or the value above which the algorithm is executed) can be set by the user of the system, or it can be preset. A range of threshold thermal values can be chosen—each of which provides a level of protection against unwanted corneal burns. For example, the highest threshold thermal value in the range can be set at a value that provides a small difference (e.g. one degree F.) between the temperature at which the cornea burns and the threshold. A lower threshold thermal value can be set so that the difference between the temperature at which the cornea burns and the threshold is much greater (10 degrees F. or so).

Regardless of the threshold chosen, the algorithm is executed when the calculated thermal value is above the threshold thermal value. When the calculated thermal value falls below the threshold, the algorithm stops executing. In this manner, the algorithm turns on and off as the calculated thermal value exceeds and falls below the threshold thermal value.

Figure 5:
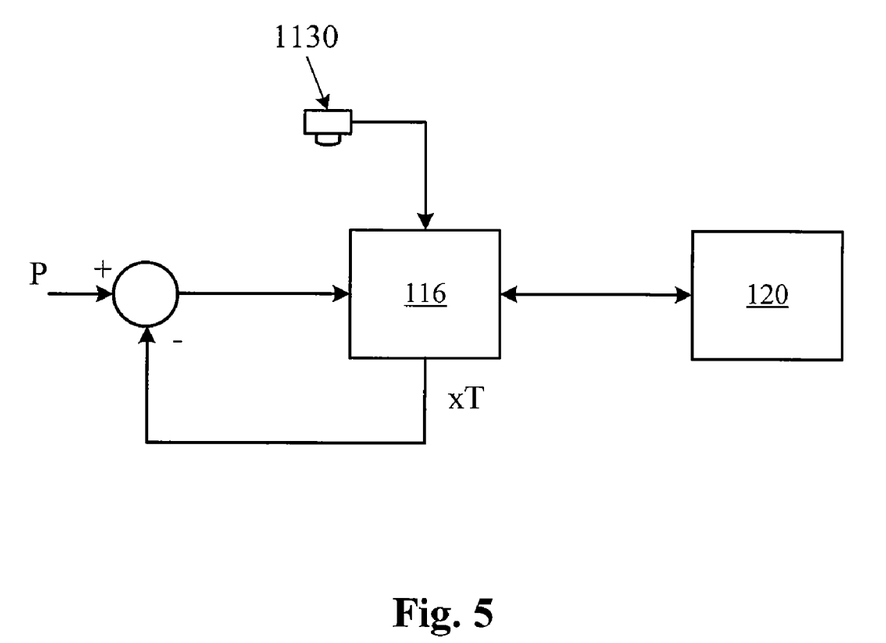
FIG. 5 is a block diagram of another embodiment of a control system according to the principles of the present invention.

FIG. 5 is a block diagram of another embodiment of a control system according to the principles of the present invention. FIG. 5 more clearly shows the algorithm in operation. CPU 116 calculates the calculated thermal value based on a reading from the irrigation pressure sensor 1130, the power from the power source 120, and the estimated friction. In FIG. 5, CPU 116 acts like a PID controller (and instead of CPU 116, a PID controller or other similar type of controller can be used). The inverse of the scaled calculated thermal value is subtracted from the power to reduce the power applied to the hand piece. In this manner, CPU 116 controls the output of power source 120 by decreasing the amount of power output by power source 120 by an amount that is inversely proportional to the calculated thermal value (or by an amount that is inversely proportional to the thermal value in excess of the threshold)—designated by xT—where x can be a scalar or a function.

In this manner, when the calculated thermal value exceeds the threshold thermal value, the power supplied to the hand piece is decreased in proportion to an amount that is in excess of the threshold thermal value. When the calculated thermal value falls below the threshold thermal value, normal operation resumes.

This implementation of the thermal watch algorithm can be set to run automatically during cataract surgery. During surgery, the doctor controls the application of power to the hand piece (generally via a foot pedal). When the calculated thermal value exceeds the threshold thermal value, the thermal watch algorithm overrides the doctor's control of power. When the calculated thermal value falls below the threshold thermal value, the doctor's control of power is resumed.

Figure 6:
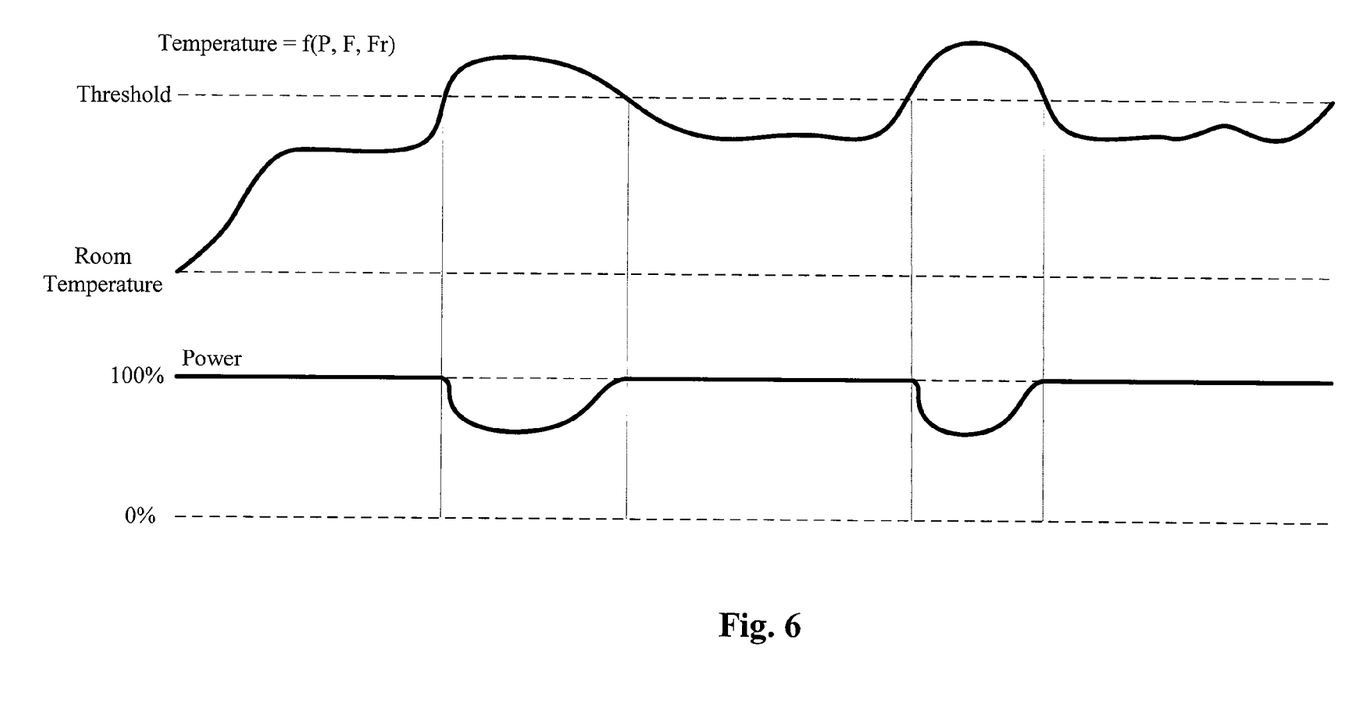
FIG. 6 is a graph depicting an exemplary operation of the thermal management algorithm in continuous mode according to the principles of the present invention.

FIG. 6 is a graph depicting an exemplary operation of the thermal management algorithm in continuous mode according to the principles of the present invention. In FIG. 6, the top graph indicates calculated thermal value, and the bottom graph indicates power applied to the hand piece. When the calculated thermal value is below the threshold thermal value, the surgeon can apply continuous power to the hand piece. In this case, the surgeon applies 100% power to the hand piece. However, the surgeon can apply any power level by depressing the foot switch. In continuous mode, power is applied continuously to the hand piece while the foot pedal is depressed. The degree to which the foot pedal is depressed (or the position of the foot pedal) determines the amount of power or power level applied. When the calculated thermal value exceeds the threshold thermal value, the thermal watch algorithm overrides the surgeon's control of power. In this manner, the thermal watch algorithm acts to decrease the power in proportion to the temperature rise over the threshold thermal value. In other words, an incremental temperature increase over the threshold thermal value results in a proportional decrease in the amount of power applied to the hand piece. The decrease in power can be smooth as depicted in FIG. 6. In this manner, a smooth decrease in power still results in power being applied smoothly to the cutting tip of the hand piece. When the power is decreased, the calculated thermal value will tend to decrease as well. When the calculated thermal value falls below the threshold thermal value, the surgeon resumes control of power—in this case, power applied returns to 100%.

Figure 7:
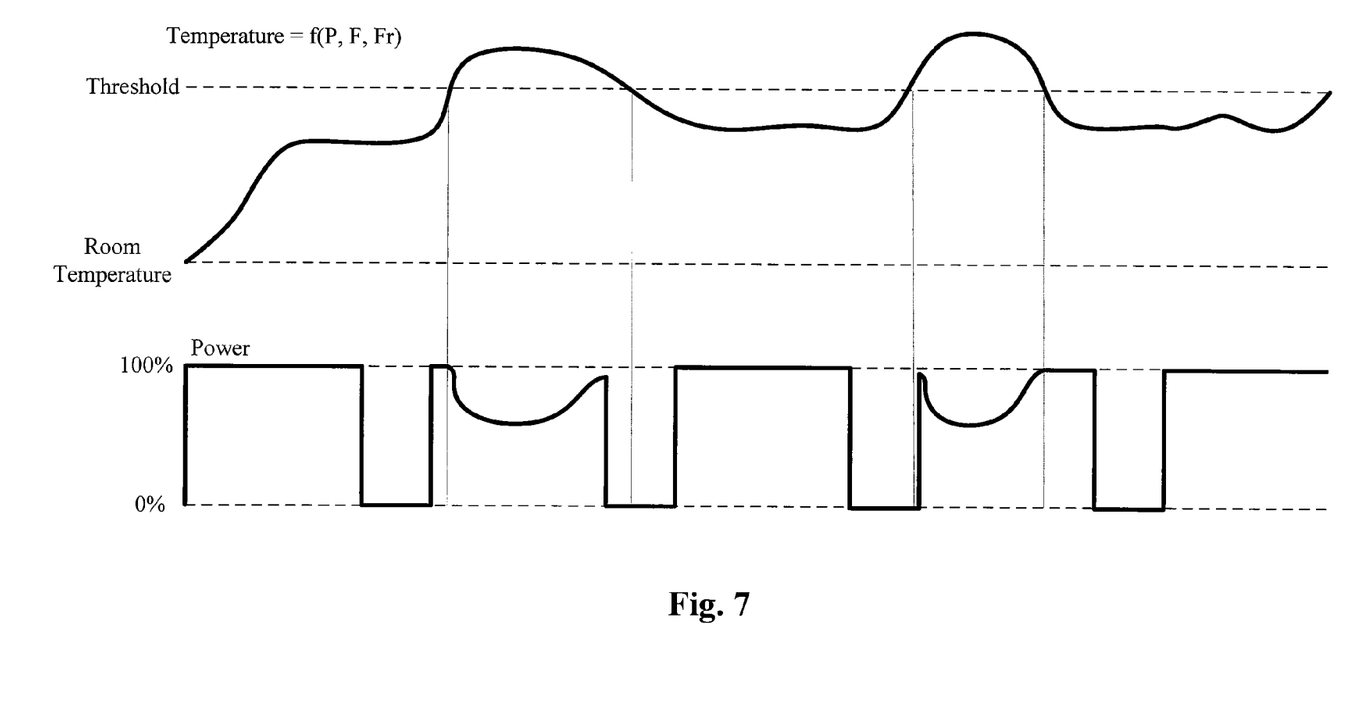
FIG. 7 is a graph depicting an exemplary operation of the thermal management algorithm in pulse mode according to the principles of the present invention.

FIG. 7 is a graph depicting an exemplary operation of the thermal management algorithm in pulse mode according to the principles of the present invention. In FIG. 7, the top graph indicates calculated thermal value, and the bottom graph indicates power applied to the hand piece. In pulse mode, a series of fixed width pulses is applied to the hand piece. The surgeon controls the amplitude (or power level) of the pulses with the foot switch. In this manner, the position of the footswitch determines the power level of the pulses. When the calculated thermal value is below the threshold thermal value, the surgeon can apply any desired power to the hand piece. In this case, the surgeon applies 100% power to the hand piece. When the calculated thermal value exceeds the threshold thermal value, the thermal watch algorithm overrides the surgeon's control of power. In this manner, the thermal watch algorithm acts to decrease the power in proportion to the temperature rise over the threshold thermal value. In other words, an incremental temperature increase over the threshold thermal value results in a proportional decrease in the amount of power applied to the hand piece. The decrease in power can be smooth as depicted in FIG. 7. In this manner, a smooth decrease in power still results in power being applied smoothly to the cutting tip of the hand piece. When the power is decreased, the calculated thermal value will tend to decrease as well. When the calculated thermal value falls below the threshold thermal value, the surgeon resumes control of power—in this case, power applied returns to 100%. As shown in FIG. 7, the thermal watch algorithm operates to decrease the power of any given pulse non-linearly. In this manner, the thermal watch algorithm operates on an individual pulse (or a series of pulses as the case may be).

Figure 8:
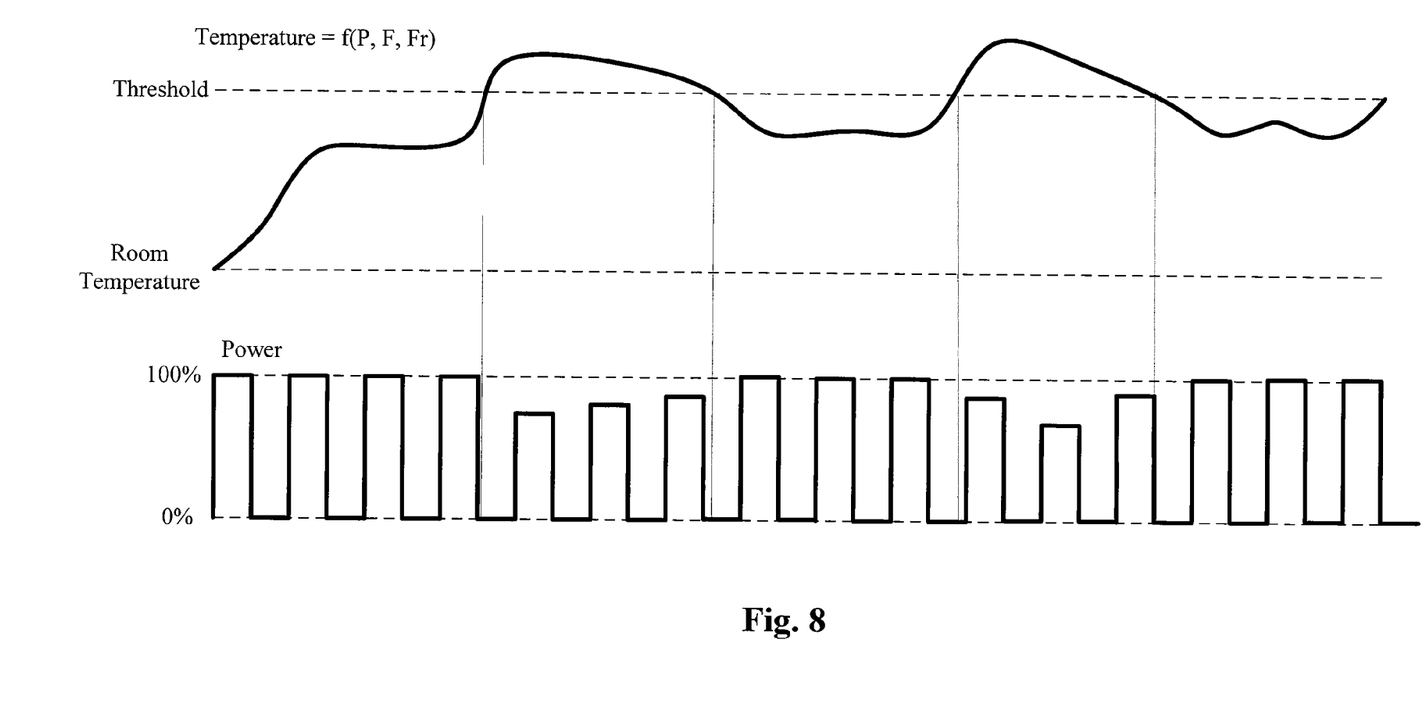
FIG. 8 is a graph depicting an exemplary operation of the thermal management algorithm in pulse mode according to the principles of the present invention.

FIG. 8 is a graph depicting an exemplary operation of the thermal management algorithm in pulse mode according to the principles of the present invention. In FIG. 8, the top graph indicates calculated thermal value, and the bottom graph indicates power applied to the hand piece. In pulse mode, a series of fixed width pulses is applied to the hand piece. The surgeon controls the amplitude (or power level) of the pulses with the foot switch. In this manner, the position of the footswitch determines the power level of the pulses. When the calculated thermal value is below the threshold thermal value, the surgeon can apply any desired power to the hand piece. In this case, the surgeon applies 100% power to the hand piece. When the calculated thermal value exceeds the threshold thermal value, the thermal watch algorithm overrides the surgeon's control of power. In this manner, the thermal watch algorithm acts to decrease the power in proportion to the temperature rise over the threshold thermal value. In other words, an incremental temperature increase over the threshold thermal value results in a proportional decrease in the amount of power applied to the hand piece. The decrease in power can be incremental as depicted in FIG. 8. In this manner, an incremental decrease in power still results in power being applied to the cutting tip of the hand piece. When the power is decreased, the calculated thermal value will tend to decrease as well. When the calculated thermal value falls below the threshold thermal value, the surgeon resumes control of power—in this case, power applied returns to 100%. As shown in FIG. 8, the thermal watch algorithm operates to decrease the power of the next pulse while maintaining a constant pulse level. In this manner, the thermal watch algorithm operates on the next pulse and serves to limit the power level of that next pulse to a constant power level.

Figure 9:
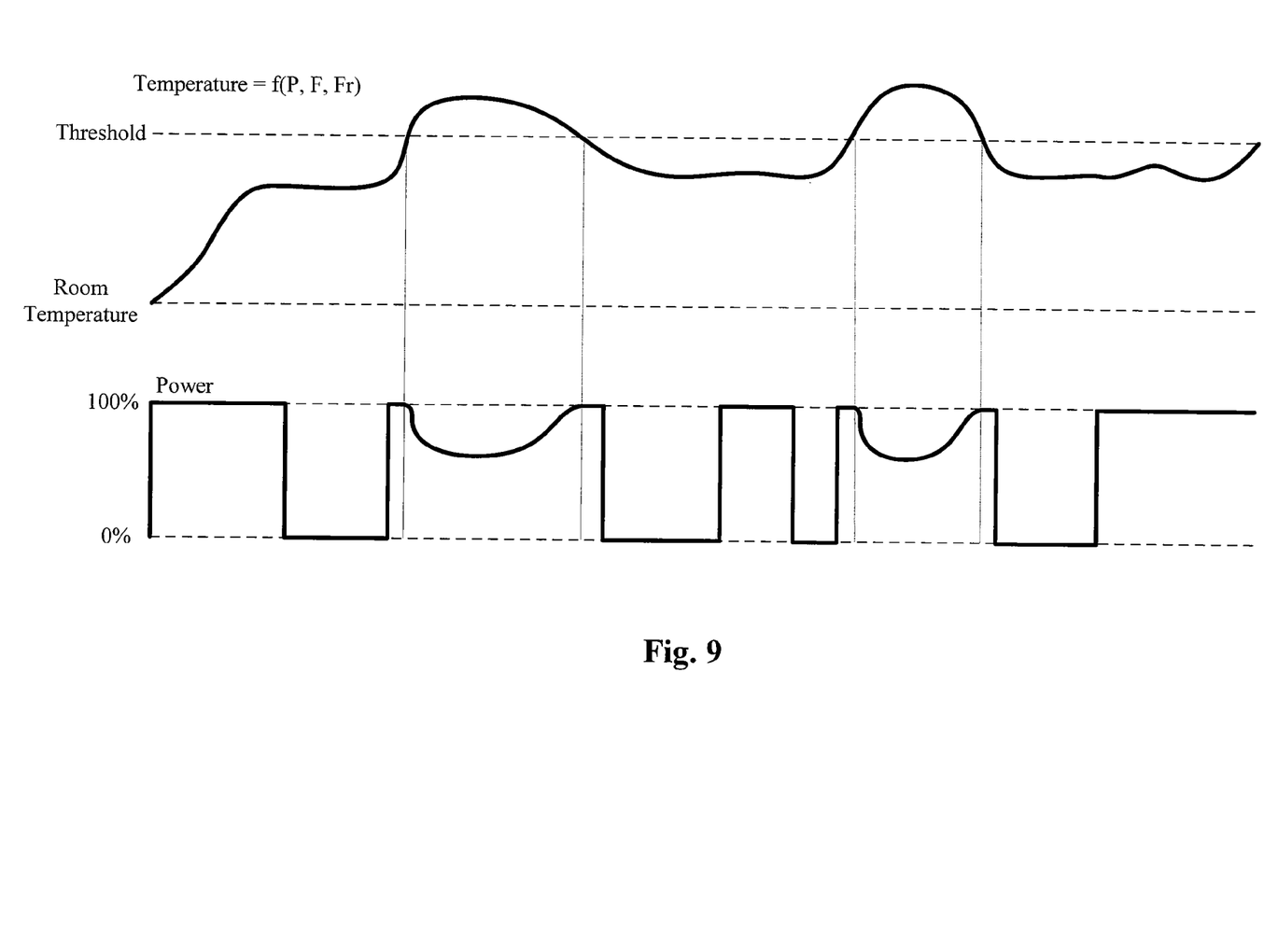
FIG. 9 is a graph depicting an exemplary operation of the thermal management algorithm in burst mode according to the principles of the present invention.

FIG. 9 is a graph depicting an exemplary operation of the thermal management algorithm in burst mode according to the principles of the present invention. In FIG. 9, the top graph indicates calculated thermal value, and the bottom graph indicates power applied to the hand piece. In burst mode, a series of pulses is applied to the hand piece. The surgeon controls the off time between pulses with the foot switch. In this manner, the position of the footswitch determines the off time between the pulses. When the calculated thermal value is below the threshold thermal value, the surgeon can apply any desired power to the hand piece. In this case, the surgeon applies 100% power to the hand piece. When the calculated thermal value exceeds the threshold thermal value, the thermal watch algorithm overrides the surgeon's control of power. In this manner, the thermal watch algorithm acts to decrease the power in proportion to the temperature rise over the threshold thermal value. In other words, an incremental temperature increase over the threshold thermal value results in a proportional decrease in the amount of power applied to the hand piece. The decrease in power can be smooth as depicted in FIG. 9. In this manner, a smooth decrease in power still results in power being applied smoothly to the cutting tip of the hand piece. When the power is decreased, the calculated thermal value will tend to decrease as well. When the calculated thermal value falls below the threshold thermal value, the surgeon resumes control of power—in this case, power applied returns to 100%. As shown in FIG. 9, the thermal watch algorithm operates to decrease the power of any given pulse non-linearly. In this manner, the thermal watch algorithm operates on an individual pulse (or a series of pulses as the case may be).

Figure 10:
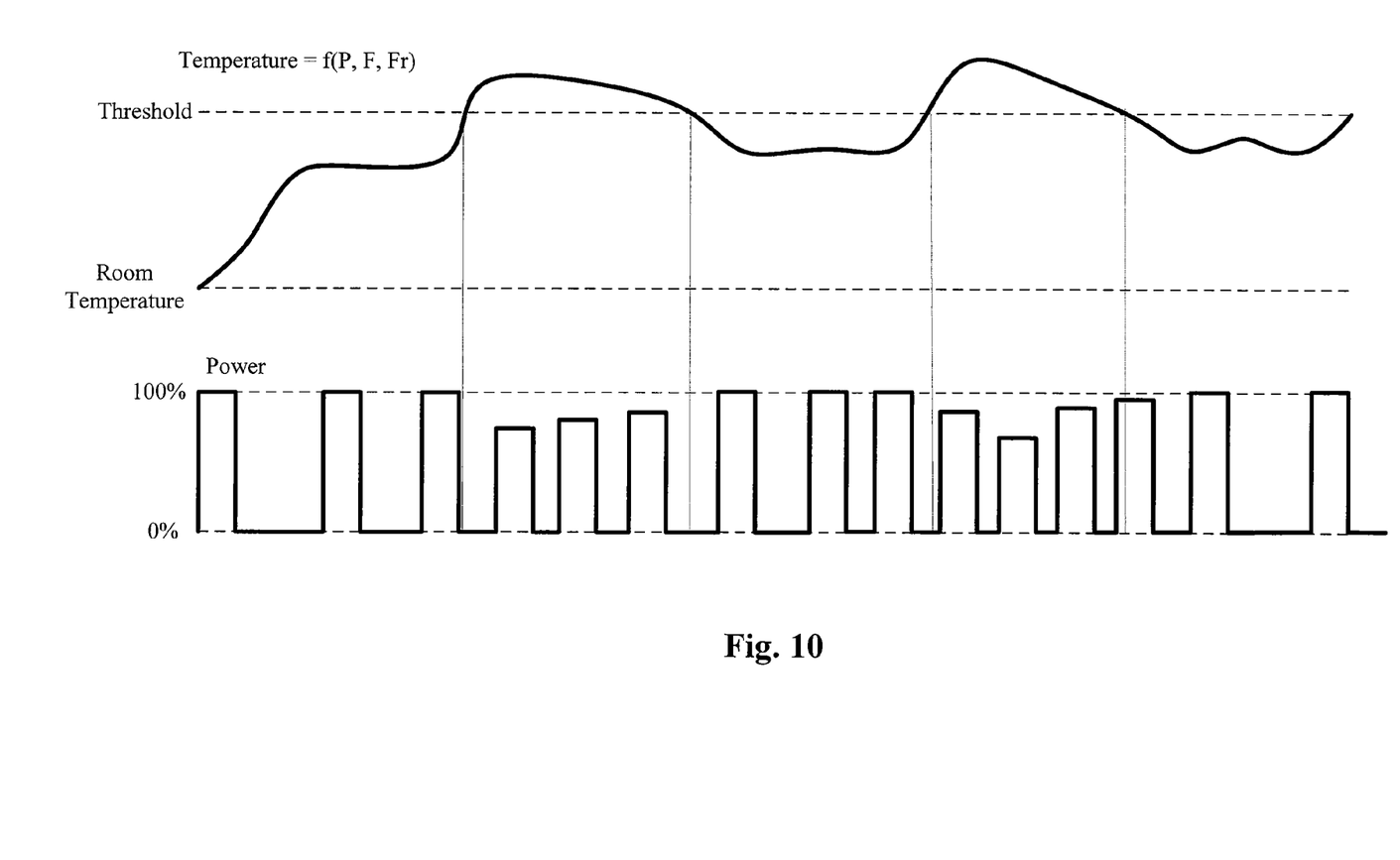
FIG. 10 is a graph depicting an exemplary operation of the thermal management algorithm in burst mode according to the principles of the present invention.

FIG. 10 is a graph depicting an exemplary operation of the thermal management algorithm in burst mode according to the principles of the present invention. In FIG. 10, the top graph indicates calculated thermal value, and the bottom graph indicates power applied to the hand piece. In burst mode, a series of pulses is applied to the hand piece. The surgeon controls the off time between pulses with the foot switch. In this manner, the position of the footswitch determines the off time between the pulses. When the calculated thermal value is below the threshold thermal value, the surgeon can apply any desired power to the hand piece. In this case, the surgeon applies 100% power to the hand piece. When the calculated thermal value exceeds the threshold thermal value, the thermal watch algorithm overrides the surgeon's control of power. In this manner, the thermal watch algorithm acts to decrease the power in proportion to the temperature rise over the threshold thermal value. In other words, an incremental temperature increase over the threshold thermal value results in a proportional decrease in the amount of power applied to the hand piece. The decrease in power can be incremental as depicted in FIG. 10. In this manner, an incremental decrease in power still results in power being applied to the cutting tip of the hand piece. When the power is decreased, the calculated thermal value will tend to decrease as well. When the calculated thermal value falls below the threshold thermal value, the surgeon resumes control of power—in this case, power applied returns to 100%. As shown in FIG. 10, the thermal watch algorithm operates to decrease the power of the next pulse while maintaining a constant pulse level. In this manner, the thermal watch algorithm operates on the next pulse and serves to limit the power level of that next pulse to a constant power level.

Several variations of the algorithm may also be implemented. In one variation, the power is decreased in proportion to a scalar factor of the temperature increase. In another variation, the power is decreased in proportion to a function of the temperature increase. In another variation, a minimum power level can be set. In this case, power will never fall below the minimum power level thus resulting in a continuous (albeit lower) application of power to the hand piece. In yet another variation, the rate at which power is decreased can be changed. In this case, the power decrease can be made to be as smooth as desired. A smooth decrease in power results in more effective cutting (as power is applied continuously and not turned off) and better surgeon feel.

From the above, it may be appreciated that the present invention provides a thermal management algorithm for phacoemulsification surgery. The present invention provides a control system that calculates a thermal value, compares the thermal value to a threshold thermal value, and reduces power supplied to the hand piece when the calculated thermal value exceeds the threshold thermal value. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A control system for managing power supplied to a phacoemulsification hand piece, the control system comprising:
   an irrigation pressure sensor for measuring an irrigation pressure;
   a power source for providing ultrasonic power to the hand piece; and
   a controller for controlling the power source;
   wherein the controller uses a thermal value calculated from the irrigation pressure and a power level to decrease the power level in proportion to the calculated thermal value when the calculated thermal value exceeds a threshold thermal value, such that the power level generally tracks the inverse of the calculated thermal value when the calculated thermal value exceeds the threshold value.

2. The control system of claim 1 wherein the calculated thermal value is provided as a feedback input to the controller.

3. The control system of claim 1 wherein the controller operates so that the power level tracks an inverse of a segment of the calculated thermal value that exceeds the threshold thermal value.

4. The control system of claim 1 wherein the controller decreases the power level smoothly.

5. The control system of claim 1 wherein the thermal value is further calculated from a friction coefficient that represents friction between an irrigation sleeve and a phacoemulsification needle, in addition to the irrigation pressure and the power level.

6. The control system of claim 1 wherein controller further compares the calculated thermal value to the threshold thermal value.

7. The control system of claim 1 wherein when the controller decreases the power level in proportion to the calculated thermal value, the controller overrides surgeon control of the power source.

8. The control system of claim 1 wherein when the controller decreases the power level in proportion to the calculated thermal value, the controller does not decrease the power level to zero.

9. The control system of claim 1 wherein the power source provides pulsed power to the hand piece and when the controller decreases the power level in proportion to the calculated thermal value, the controller decreases the amplitude of a pulse.

10. The control system of claim 1 wherein surgeon control of the power source is resumed when the calculated thermal value is less than the threshold thermal value.

11. A control system for managing power supplied to a phacoemulsification hand piece, the control system comprising:
    a power source for providing power to the hand piece; and
    a controller for controlling the power source;
    wherein the controller uses a thermal value calculated from irrigation fluid flow and a power level to decrease the power level in proportion to the calculated thermal value when the calculated thermal value exceeds a threshold thermal value, such that the power level generally tracks the inverse of the calculated thermal value when the calculated thermal value exceeds the threshold value.

12. The control system of claim 11 wherein the calculated thermal value is provided as a feedback input to the controller.

13. The control system of claim 11 wherein the controller operates so that the power level tracks an inverse of a segment of the calculated thermal value that exceeds the threshold thermal value.

14. The control system of claim 11 wherein the controller decreases the power level smoothly.

15. The control system of claim 11 wherein the thermal value is further calculated from a friction coefficient that represents friction between an irrigation sleeve and a phacoemulsification needle, in addition to the irrigation fluid flow and the power level.

16. The control system of claim 11 wherein controller further compares the calculated thermal value to the threshold thermal value.

17. The control system of claim 11 further comprising:
    an irrigation pressure sensor that measures an irrigation pressure used by the controller to calculate the irrigation fluid flow.

18. The control system of claim 11 wherein when the controller decreases the power level in proportion to the calculated thermal value, the controller overrides surgeon control of the power source.

19. The control system of claim 11 wherein when the controller decreases the power level in proportion to the calculated thermal value, the controller does not decrease the power level to zero.

20. The control system of claim 11 wherein the power source provides pulsed power to the hand piece and when the controller decreases the power level in proportion to the calculated thermal value, the controller decreases the amplitude of a pulse.

21. The control system of claim 11 wherein surgeon control of the power source is resumed when the calculated thermal value is less than the threshold thermal value.

* * * * *